(12) United States Patent
Irisawa et al.

(10) Patent No.: US 10,849,507 B2
(45) Date of Patent: Dec. 1, 2020

(54) PHOTOACOUSTIC IMAGE GENERATION APPARATUS AND INSERT

(71) Applicant: FUJIFILM Corporation, Tokyo (JP)

(72) Inventors: Kaku Irisawa, Kanagawa (JP); Tomoki Inoue, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 359 days.

(21) Appl. No.: 15/902,233

(22) Filed: Feb. 22, 2018

(65) Prior Publication Data
US 2018/0177409 A1 Jun. 28, 2018

Related U.S. Application Data

(63) Continuation of application No. PCT/JP2016/003797, filed on Aug. 22, 2016.

(30) Foreign Application Priority Data

Aug. 31, 2015 (JP) .................. 2015-170513

(51) Int. Cl.
*A61B 5/00* (2006.01)
*A61B 1/06* (2006.01)
(Continued)

(52) U.S. Cl.
CPC .......... *A61B 5/0095* (2013.01); *A61B 1/0638* (2013.01); *A61B 1/07* (2013.01);
(Continued)

(58) Field of Classification Search
CPC .......... A61B 5/00; A61B 1/0638; A61B 1/07; A61B 5/0035; A61B 5/6848; A61B 8/12; A61B 5/0095; A61B 8/13; A61B 8/5261
See application file for complete search history.

(56) References Cited

U.S. PATENT DOCUMENTS 6,366,726 B1 * 4/2002 Wach .................. G01N 21/474
385/115
2008/0108867 A1 * 5/2008 Zhou .................. A61B 5/02007
600/104
(Continued)

FOREIGN PATENT DOCUMENTS

JP 2013-13713 A 1/2013
JP 5243056 B2 7/2013
(Continued)

OTHER PUBLICATIONS

Wei ["Integrated ultrasound and photoacoustic probe for co-registered intravascular maging" Journal of Biomedical Optics 16(10), 106001 (Oct. 2011) ] (Year: 2011).*
(Continued)

*Primary Examiner* — Oommen Jacob
(74) *Attorney, Agent, or Firm* — Birch, Stewart, Kolasch & Birch, LLP

(57) ABSTRACT

Present disclosure provides an insert that is at least partially inserted into a subject, the insert includes: a first light guide member that guides light with a first wavelength; a first light emitting portion from which the light guided by the first light guide member is emitted; a second light guide member that is provided so as to be adjacent to the first light guide member and guides light with a second wavelength different from the first wavelength; a second light emitting portion from which the light guided by the second light guide member is emitted; and a light absorption/conversion member.

10 Claims, 8 Drawing Sheets

(51) Int. Cl.
*A61B 1/07* (2006.01)
*A61B 8/12* (2006.01)
*A61B 8/13* (2006.01)
*A61B 8/08* (2006.01)

(52) U.S. Cl.
CPC .......... *A61B 5/0035* (2013.01); *A61B 5/6848* (2013.01); *A61B 8/12* (2013.01); *A61B 8/13* (2013.01); *A61B 8/5261* (2013.01)

(56) References Cited

U.S. PATENT DOCUMENTS

| | | | |
|---|---|---|---|
| 2009/0002685 A1 | 1/2009 | Fukutani et al. | |
| 2009/0156932 A1* | 6/2009 | Zharov | A61B 5/0059 600/437 |
| 2012/0029829 A1* | 2/2012 | Li | A61B 5/0059 702/19 |
| 2012/0271170 A1* | 10/2012 | Emelianov | A61B 5/0095 600/439 |
| 2013/0096422 A1* | 4/2013 | Boctor | A61B 5/0095 600/424 |
| 2014/0066743 A1* | 3/2014 | Nakajima | A61B 5/0095 600/407 |
| 2014/0076055 A1* | 3/2014 | Asao | G01H 9/00 73/655 |
| 2014/0180056 A1* | 6/2014 | Hoseit | A61B 5/6851 600/407 |
| 2014/0200454 A1* | 7/2014 | Li | A61B 8/44 600/443 |
| 2014/0277294 A1* | 9/2014 | Jones | A61N 5/062 607/88 |
| 2014/0288351 A1* | 9/2014 | Jones | A61N 5/06 600/9 |
| 2015/0038824 A1* | 2/2015 | Lupotti | A61B 18/1492 600/407 |
| 2015/0208925 A1 | 7/2015 | Bagwell et al. | |
| 2015/0297092 A1 | 10/2015 | Irisawa | |
| 2018/0177408 A1* | 6/2018 | Irisawa | A61B 8/4416 |
| 2018/0177409 A1* | 6/2018 | Irisawa | A61B 1/0638 |

FOREIGN PATENT DOCUMENTS

| | | |
|---|---|---|
| JP | 2014-223547 A | 12/2014 |
| JP | 2015-37519 A | 2/2015 |

OTHER PUBLICATIONS

Guo ["Photoacoustic active ultrasound element for catheter tracking"], Proc. SPIE 8943, Photons Plus Ultrasound: Imaging and Sensing 2014, 89435M (Mar. 3, 2014) (Year: 2014).*
Japanese Office Action, dated Jul. 31, 2018 for corresponding Japanese Application No. 2017-537213, with an English machine translation.
International Preliminary Report on Patentability and Written Opinion of the International Searching Authority (Forms PCT/IB/326, PCT/IB/373 and PCT/ISA/237) for Application No. PCT/JP2016/003797, dated Mar. 15, 2018, with an English translation.
International Search Report and English translation (Form PCT/ISA/210) for Application No. PCT/JP2016/003797, dated Dec. 20, 2016.

* cited by examiner

PHOTOACOUSTIC IMAGE GENERATION APPARATUS AND INSERT

CROSS-REFERENCE TO RELATED APPLICATIONS

This application is a continuation application of International Application No. PCT/JP2016/003797, filed Aug. 22, 2016, the disclosure of which is incorporated herein by reference in its entirety. Further, this application claims priority from Japanese Patent Application No. 2015-170513 filed on Aug. 31, 2015, the disclosure of which is incorporated herein by reference in its entirety.

BACKGROUND

Technical Field

The present disclosure relates to a photoacoustic image generation apparatus, and more particularly, to a photoacoustic image generation apparatus that detects photoacoustic waves generated by the absorption of light by a light absorber and generates a photoacoustic image.

In addition, the present disclosure relates to an insert such as a puncture needle used in the photoacoustic image generation apparatus.

Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

For the photoacoustic imaging, JP2015-37519A discloses a technique in which light emitted from a light source is guided to the vicinity of a leading end of a puncture needle by, for example, an optical fiber and is emitted from the leading end to a photoacoustic wave generation portion of the puncture needle. The photoacoustic wave generation portion includes, for example, a light absorption member. JP2015-37519A discloses a technique in which the light absorption member can be made of, for example, an epoxy resin, a polyurethane resin, or a fluorine resin with which a black pigment is mixed, silicon rubber, or a black paint having high light absorbance with respect to the wavelength of laser light. In addition, JP2015-37519A discloses a technique in which a metal film or an oxide film having light absorptivity with respect to the wavelength of laser light is used as the light absorption member. An ultrasound probe detects the photoacoustic waves generated by the emission of light to the photoacoustic wave generation portion and a photoacoustic image is generated on the basis of a detection signal of the photoacoustic waves. In the photoacoustic image, a part of the photoacoustic wave generation portion appears as a bright point, which makes it possible to check the position of the puncture needle using the photoacoustic image.

Furthermore, JP2013-13713A discloses a puncture needle including a light emitting portion. In JP2013-13713A, light emitted from a light source is guided to the light emitting portion of the puncture needle by, for example, an optical fiber and is emitted from the light emitting portion to the outside.

In a subject, photoacoustic waves are generated due to the absorption of the light emitted from the light emitting portion. An ultrasound probe detects the photoacoustic waves generated by the absorption of the light emitted from the light emitting portion of the puncture needle and a photoacoustic image is generated on the basis of the detection signal of the photoacoustic waves. In this way, it is possible to check the position of the puncture needle.

In JP2015-37519A, the light absorber provided at the leading end of the needle generates photoacoustic waves and the light absorber absorbs almost all of the light emitted to the photoacoustic wave generation portion. Therefore, even in a situation in which the light absorber is present in front of the needle in a needling direction in the subject, it is difficult for the light absorber to generate photoacoustic waves. For this reason, in JP2015-37519A, only the positional information of the tip of the needle can be acquired and it is difficult to acquire surrounding environment information such as information indicating whether the light absorber is present in the vicinity of the needle. In contrast, in JP2013-13713A, the light absorber that is present in front of the needle in the needling direction in the subject is irradiated with the light emitted from the light emitting portion. Therefore, in a case in which light with a wavelength absorbed by blood (blood vessel) is emitted from the light emitting portion, it is possible to determine whether the tip of the needle has been inserted into the blood vessel on the basis of whether a bright point is present in the photoacoustic image. However, in JP2013-13713A, the light emitting portion is exposed from, for example, a leading end portion of the needle and it is necessary to cover the leading end of the light emitting portion with an appropriate member.

However, in JP2013-13713A, it is necessary to prepare light sources corresponding to the number of absorption wavelengths in order to evaluate whether a plurality of materials with different absorption wavelengths are present in the vicinity of the puncture needle. There is a problem that, as the number of light sources increases, the overall cost of the apparatus increases. This problem is not limited to the puncture needle and is likely to occur in a case in which the position and surrounding environment information of other inserts to be inserted into the subject, such as a catheter and a guide wire, are acquired by a photoacoustic image.

SUMMARY

The present disclosure provides a photoacoustic image generation apparatus that can acquire both positional information and surrounding environment information of an insert.

In addition, the present disclosure provides an insert that can acquire both the positional information and the surrounding environment information of the insert.

A first aspect provides an insert that is at least partially inserted into a subject. The insert includes: a first light guide member that guides light with a first wavelength; a first light emitting portion from which the light guided by the first light guide member is emitted; a second light guide member that is provided so as to be adjacent to the first light guide member and guides light with a second wavelength different from the first wavelength; a second light emitting portion from which the light guided by the second light guide member is emitted; and a light absorption/conversion member that at least partially covers light emission surfaces of the first light emitting portion and the second light emitting portion, absorbs the light with the first wavelength emitted from the first light emitting portion to generate photoacoustic waves, and converts the light with the second wavelength emitted from the second light emitting portion into light with a third wavelength different from the first wavelength and the second wavelength.

In the insert according to a second aspect, the light absorption/conversion member includes a light absorber that transmits the light with the second wavelength and the light with the third wavelength and absorbs the light with the first wavelength to generate photoacoustic waves, a phosphor that converts the light with the second wavelength into the light with the third wavelength, and a resin including the light absorber and the phosphor.

The insert according to a third aspect may have an inner cavity. In this case, the light absorption/conversion member may function as a fixing member that fixes the first light guide member and the second light guide member to an inner wall of the inner cavity of the insert.

The insert according to a fourth aspect may further include a transparent resin that transmits the light with the third wavelength. The light absorption/conversion member may be covered with the transparent resin.

The insert according to a fifth aspect may have an inner cavity. The first light guide member, the second light guide member, and the light absorption/conversion member may be fixed to an inner wall of the inner cavity of the insert by the transparent resin.

The insert according to a sixth aspect may be a puncture needle having an inner cavity. The insert may further include a hollow tube in which the first light guide member and the second light guide member are accommodated.

In a seventh aspect, the puncture needle may include an inner needle and an outer needle. The inner needle may include the hollow tube. The inner needle may seal at least a portion of the inner cavity of the puncture needle.

In the insert according to an eighth aspect, the light absorption/conversion member may function as a fixing member that fixes the first light guide member and the second light guide member to an inner wall of the hollow tube.

The insert according to a ninth aspect may further include a transparent resin that transmits the light with the third wavelength. The first light guide member, the second light guide member, and the light absorption/conversion member may be fixed to an inner wall of the hollow tube by the transparent resin.

In a tenth aspect, the first light emitting portion is provided at a center of the insert in a width direction.

In addition, an eleventh aspect provides a photoacoustic image generation apparatus including: a first light source that emits light with a first wavelength; a second light source that emits light with a second wavelength different from the first wavelength; an insert that is at least partially inserted into a subject and includes a first light guide member that guides the light with the first wavelength, a first light emitting portion from which the light guided by the first light guide member is emitted, a second light guide member that is provided so as to be adjacent to the first light guide member and guides the light with the second wavelength, a second light emitting portion from which the light guided by the second light guide member is emitted, and a light absorption/conversion member that at least partially covers light emission surfaces of the first light emitting portion and the second light emitting portion, absorbs the light with the first wavelength emitted from the first light emitting portion to generate first photoacoustic waves, and converts the light with the second wavelength emitted from the second light emitting portion into light with a third wavelength different from the first wavelength and the second wavelength; acoustic wave detection unit that detects the first photoacoustic waves and second photoacoustic waves which are generated in the subject by the emission of the light with the third wavelength to the subject; and photoacoustic image generation unit that generates a first photoacoustic image on the basis of the first photoacoustic waves, generates a second photoacoustic image on the basis of the second photoacoustic waves, and generates a third photoacoustic image on the basis of both the first photoacoustic waves and the second photoacoustic waves.

In the photoacoustic image generation apparatus according to a twelfth aspect, the acoustic wave detection unit further detects reflected acoustic waves with respect to acoustic waves transmitted to the subject. The photoacoustic image generation apparatus according to the twelfth aspect may further includes reflected acoustic image generation unit that generates a reflected acoustic image on the basis of the reflected acoustic waves.

The photoacoustic image generation apparatus according to a thirteenth aspect may further include image combination unit that combines at least one of the first photoacoustic image, the second photoacoustic image, or the third photoacoustic image and the reflected acoustic image.

The photoacoustic image generation apparatus and the insert according to the present disclosure can acquire both the positional information and the surrounding environment information of the insert.

BRIEF DESCRIPTION OF THE DRAWINGS

Figure 1:
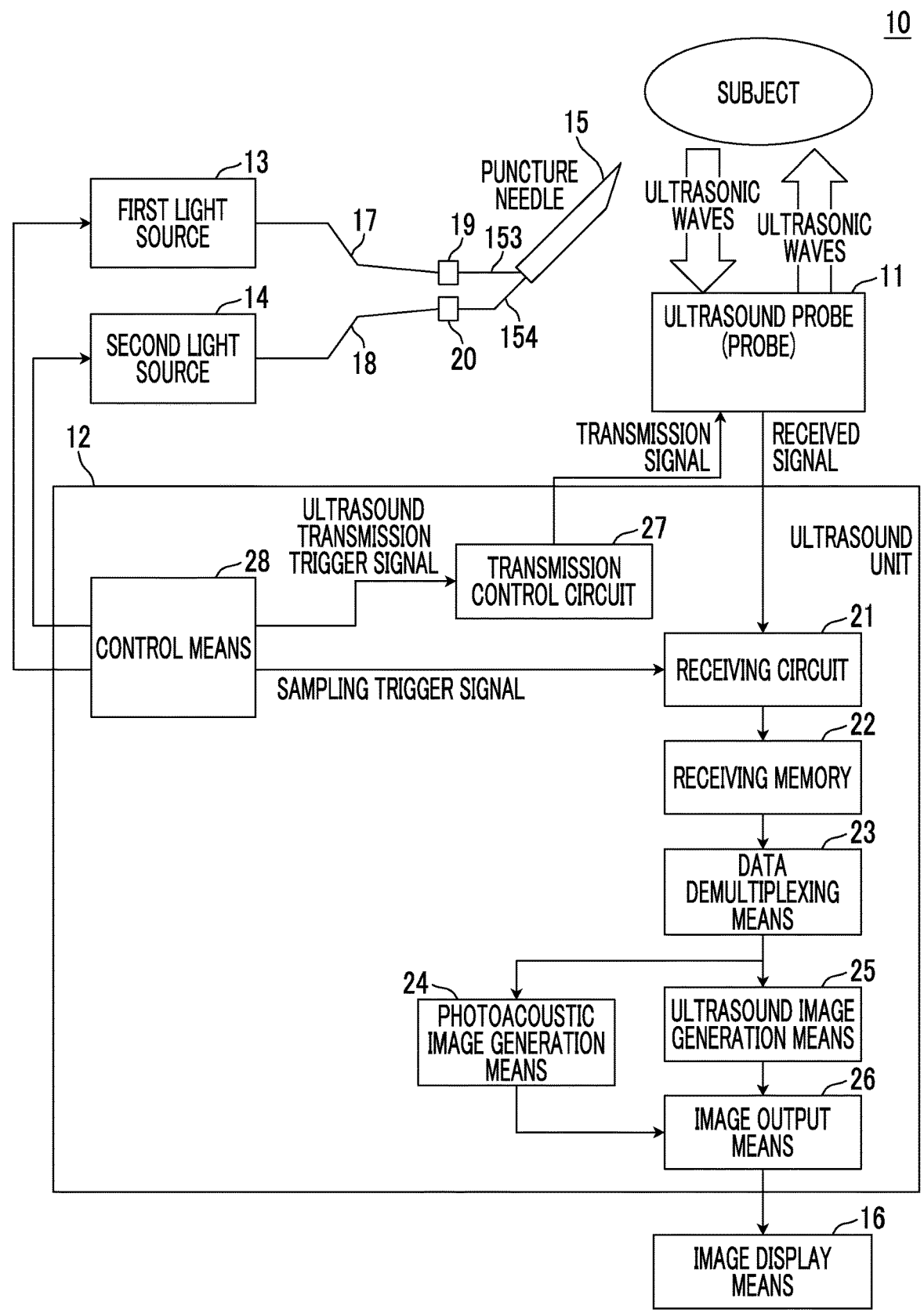
FIG. 1 is a block diagram illustrating a photoacoustic image generation apparatus according to a first embodiment.

Hereinafter, embodiments of the present disclosure will be described in detail with reference to the drawings. FIG. 1 illustrates a photoacoustic image generation apparatus according to a first embodiment of the present disclosure. A photoacoustic image generation apparatus 10 includes a probe (ultrasound probe) 11, an ultrasound unit 12, a first light source (laser unit) 13, a second light source (laser unit) 14, and a puncture needle 15. In the embodiment of the present disclosure, ultrasonic waves are used as acoustic waves. However, the present disclosure is not limited to the ultrasonic waves. Acoustic waves with an audible frequency may be used as long as an appropriate frequency can be selected according to, for example, an inspection target or measurement conditions.

The first light source 13 emits light with a first wavelength. The second light source 14 emits light with a second wavelength. For example, the first light source 13 and the second light source 14 emit pulsed light with a pulse energy of about 0.3 µJ to 30 µJ and a pulse time width of about 1 ns to 100 ns. The first wavelength and the second wavelength are different from each other. The first light source 13 and the second light source 14 are, for example, solid-state laser light sources. The type of light source is not particularly limited. The first light source 13 and the second light source 14 may be laser diode light sources (semiconductor laser light sources) or light amplifying laser light sources having a laser diode light source as a seed light source. In addition, light sources other than the laser light source may be used.

The light with the first wavelength emitted from the first light source 13 is guided to the puncture needle 15 by light guide means, such as an optical fiber 17, and a light guide member (first light guide member), such as an optical fiber 153. The light with the second wavelength emitted from the second light source 14 is guided to the puncture needle 15 by light guide means, such as an optical fiber 18, and a light guide member (second light guide member), such as an optical fiber 154.

The puncture needle 15 is a needle that is inserted into a subject. The optical fiber 153 and the optical fiber 154 are inserted into the puncture needle 15. An optical connector 19 is provided between the optical fiber 17 close to the first light source 13 and the optical fiber 153 inserted into the puncture needle 15. The optical connector 19 detachably connects the optical fiber 17 and the optical fiber 153. Similarly, an optical connector 20 is provided between the optical fiber 18 close to the second light source 14 and the optical fiber 154 inserted into the puncture needle 15. The optical connector 20 detachably connects the optical fiber 18 and the optical fiber 154. The connection of the optical connector 19 and the optical connector 20 is released to throw away the optical fiber 153 and optical fiber 154 together with the puncture needle 15 at the same time.

Figure 2:
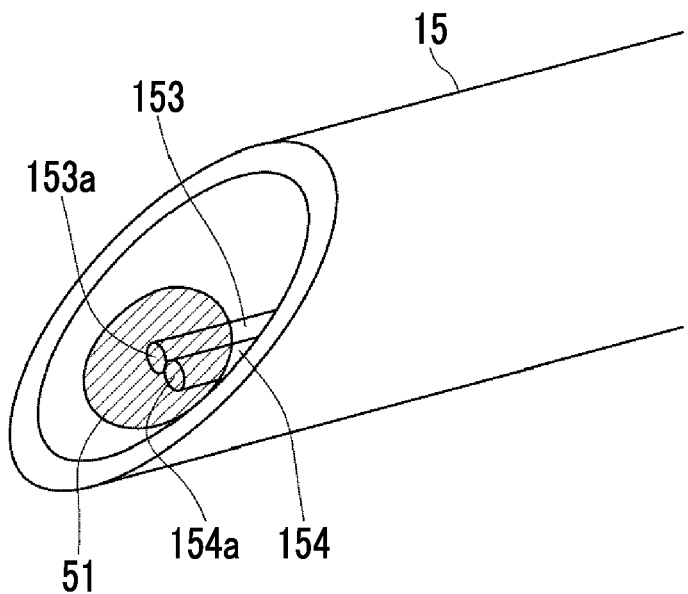
FIG. 2 is a perspective view illustrating the vicinity of a leading end of a puncture needle.

FIG. 2 illustrates the vicinity of a leading end of the puncture needle 15. The puncture needle 15 has a light absorption/conversion member 51 provided in the vicinity of the leading end. A leading end (a far end as viewed from the light source side) of the optical fiber 153 forms a light emitting portion (first light emitting portion) 153a from which guided light is emitted. A leading end of the optical fiber 154 forms a light emitting portion (second light emitting portion) 154a from which guided light is emitted. For example, the light absorption/conversion member 51 at least partially covers the light emission surfaces of the first light emitting portion 153a and the second light emitting portion 154a. The light absorption/conversion member 51 may also function as a fixing member that fixes the optical fiber 153 and the optical fiber 154 to the inner wall of an inner cavity of the puncture needle 15. The optical fiber 153 and the optical fiber 154 may be coated. For example, polyimide, a fluorine resin, or an acrylic resin may be used for coating.

The light absorption/conversion member 51 absorbs the light with the first wavelength emitted from the first light emitting portion 153a and generates photoacoustic waves. The light absorption/conversion member 51 is provided in the vicinity of the leading end of the puncture needle 15 and can generate photoacoustic waves at a point in the vicinity of the leading end of the puncture needle 15. Since the length of a generation source (sound source) of the photoacoustic waves is sufficiently smaller than the total length of the puncture needle, the sound source can be regarded as a point sound source. In addition, the light absorption/conversion member 51 absorbs the light with the second wavelength emitted from the second light emitting portion 154a and converts the light with the second wavelength into light with a third wavelength. The third wavelength is different from the first wavelength and the second wavelength.

The first light emitting portion 153a is provided in the vicinity of the leading end of the puncture needle 15. The optical fiber 153 guides the light with the first wavelength which is incident from the first light source 13 to the vicinity of the leading end of the puncture needle 15. The second light emitting portion 154a is also provided in the vicinity of the leading end of the puncture needle 15 and the optical fiber 154 guides the light with the second wavelength which is incident from the second light source 14 to the vicinity of the leading end of the puncture needle 15. Here, "the vicinity of the leading end" means a position where the light absorption/conversion member 51 provided at the leading end can generate photoacoustic waves capable of imaging the position of the leading end of the puncture needle 15 with accuracy required for a needling operation in a case in which the light emitting portion 153a and the light emitting portion 154a are disposed at the position. For example, the vicinity of the leading end is the range of 0 mm to 3 mm from the leading end to the base end of the puncture needle 15.

In the puncture needle 15, the optical fiber 154 is provided so as to be adjacent to the optical fiber 153. Here, the term "being disposed so as to be adjacent" means, for example, that the optical fiber 153 and the optical fiber 154 are arranged side by side in the width direction of the puncture needle 15. For example, the optical fiber 153 and the optical fiber 154 are arranged side by side in an aspect in which there is a clearly visible gap therebetween. Alternatively, there may be no gap between the optical fiber 153 and the optical fiber 154.

The light absorption/conversion member 51 includes, for example, a light absorber that absorbs light with the first wavelength and transmits light with the second wavelength and light with the third wavelength, a phosphor that emits light with the third wavelength using light with the second wavelength as excitation light, and a resin (for example, an epoxy resin) including the light absorber and the phosphor. For example, in a case in which a pulsed laser diode with a wavelength of 905 nm is used as the first light source 13, a material that absorbs light with the wavelength is mixed as the light absorber with a resin. For example, the following material can be used as the light absorber: YKR-2900 or YKR-2081 which is a phthalocyanine-based material manufactured by Yamamoto Chemical Industry Co., Ltd.; FDN-004 or FDN-005 manufactured by Yamada Chemical Co., Ltd.; a cyanine-based absorber material disclosed in JP5243056B; IRA908, IRA912, or IRA931 manufactured by Exciton Inc.; or S0433 manufactured by FEW Chemicals GmbH. In a case in which these absorbers are used, a pulsed laser diode with a wavelength of 870 nm may be used as the first light source 13.

It is preferable that the phosphor included in the light absorption/conversion member 51 emits light, for example, in a nanosecond order. For example, a quantum dot or an organic phosphor (organic pigment) is used as the phosphor. It is preferable that the quantum dot is a PbS-based quantum dot. For example, a quantum dot manufactured by Evident Technologies Inc. is used.

In a case in which the light absorber transmits light with the second wavelength and light with the third wavelength, the light absorber does not need to transmit all of the light with the second wavelength and the light with the third wavelength. That is, the light absorbance of the light absorber does not need to be 0%. The light absorber may absorb and transmit each of the light with the second wavelength and the light with the third wavelength at a ratio of, for example, about 1:9. Similarly, in a case in which the light absorber absorbs the light with the first wavelength, the light absorber does not need to absorb all of the light with the first wavelength. That is, the light absorbance of the light absorber does not need to be 100%. The light absorber may absorb and transmit the light with the first wavelength at a ratio of, for example, about 9:1.

In a case in which a resin including the absorber and the phosphor is used as the light absorption/conversion member 51, the light with the first wavelength emitted from the first light source 13 is converted into acoustic waves. The acoustic waves (photoacoustic waves) can be used to detect the position of the leading end of the puncture needle 15.

Figure 3:
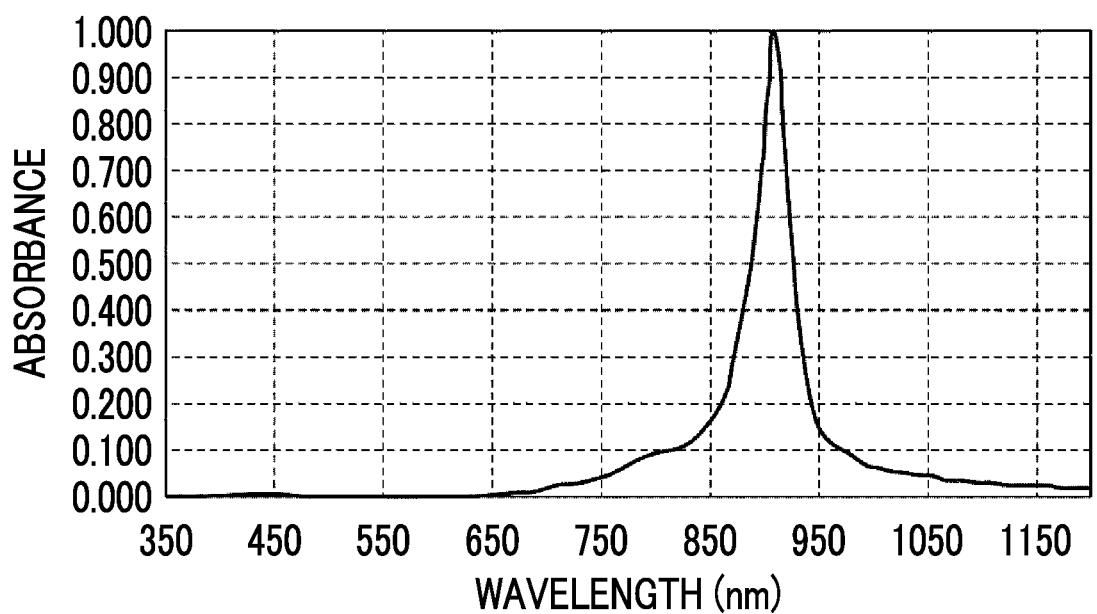
FIG. 3 is a graph illustrating an example of an absorption spectrum of a light absorption/conversion member.

FIG. 3 illustrates an example of the absorption spectrum of the light absorber included in the light absorption/conversion member 51. The horizontal axis indicates a wavelength and the vertical axis indicates absorbance. A cyanine-based absorber material is used as the light absorber included in the absorber included in the light absorption/conversion member 51. In the light absorption/conversion member 51, the absorbance of light with a wavelength of about 905 nm is the highest and the absorbance of light is rapidly reduced toward a long wavelength side and a short wavelength side. In a case in which the light absorption/conversion member 51 is used, the wavelength of the light emitted from the second light source 14 may be appropriately selected from the range of 400 nm to 650 nm or the range of 1000 nm or more.

The first light source 13 is not limited to the light source that emits only the light with the first wavelength. A light source that can emit light components with a plurality of wavelengths may be used as the first light source 13. An example of the light source that can emit light components with a plurality of wavelengths including the first wavelength (905 nm) is a Ti:Sf laser or a Nd:YAG-optical parametric oscillation (OPO) laser.

The light with the second wavelength emitted from the second light source 14 is converted into light with the third wavelength by the light absorption/conversion member 51 and is then emitted to the outside of the puncture needle 15. That is, the light with the third wavelength is emitted to the outside of the puncture needle 15. In a case in which an absorber that absorbs the light with the third wavelength is present in the emission range of the light with the third wavelength, photoacoustic waves are generated from the absorber. The third wavelength is, for example, a wavelength indicating absorptivity in the light absorbance-wavelength characteristics of a material (evaluation target material) present at a needling target position of the puncture needle 15.

The phosphor included in the light absorption/conversion member 51 is selected according to a material that is present in the vicinity of the position where the puncture needle 15 is inserted. In other words, the phosphor is selected according to an evaluation target material in the surrounding environment of the puncture needle 15. For example, in a case in which the evaluation target material is a nerve, a phosphor that converts light (excitation light) with the second wavelength into light with a wavelength of 1210 nm is selected as the phosphor included in the light absorption/conversion member 51. For example, a PbS-based phosphor is used as the phosphor.

In a case in which the evaluation target material is a contrast agent used to visualize, for example, a lymph node or a lymph tube, a phosphor that converts the light with the second wavelength into light with a wavelength (third wavelength) which is absorbed by the contrast agent to generate photoacoustic waves may be used as the phosphor included in the light absorption/conversion member 51. For example, in a case in which indocyanine green (ICG) is used as the contrast agent, a phosphor that converts excitation light into light with a wavelength of 800 nm may be used. An example of this phosphor is PbS or CdTe. In a case in which methylene blue and Patent Blue V are used as the contrast agents, a phosphor that converts excitation light into light with a wavelength of 650 nm may be used since the absorption peaks of methylene blue and Patent Blue V are 663 nm and 638 nm, respectively. An example of this phosphor is InP/ZnS.

In a case in which a specific material is transferred to a cancer cell by a drug delivery system (DDS) and the user wants to evaluate the material as the evaluation target material, a phosphor that converts the light with the second wavelength into light with a wavelength (third wavelength) which is absorbed by the material to generate photoacoustic waves may be used as the phosphor included in the light absorption/conversion member 51. For example, in a case in which the evaluation target is a gold nanoparticle, a phosphor that converts excitation light into light with a wavelength selected from a wavelength range of 600 nm to 900 nm according to the diameter of the gold nanoparticle may be used. For example, CdTe is used as the phosphor that emits light with a wavelength of 770 nm.

Figure 4:
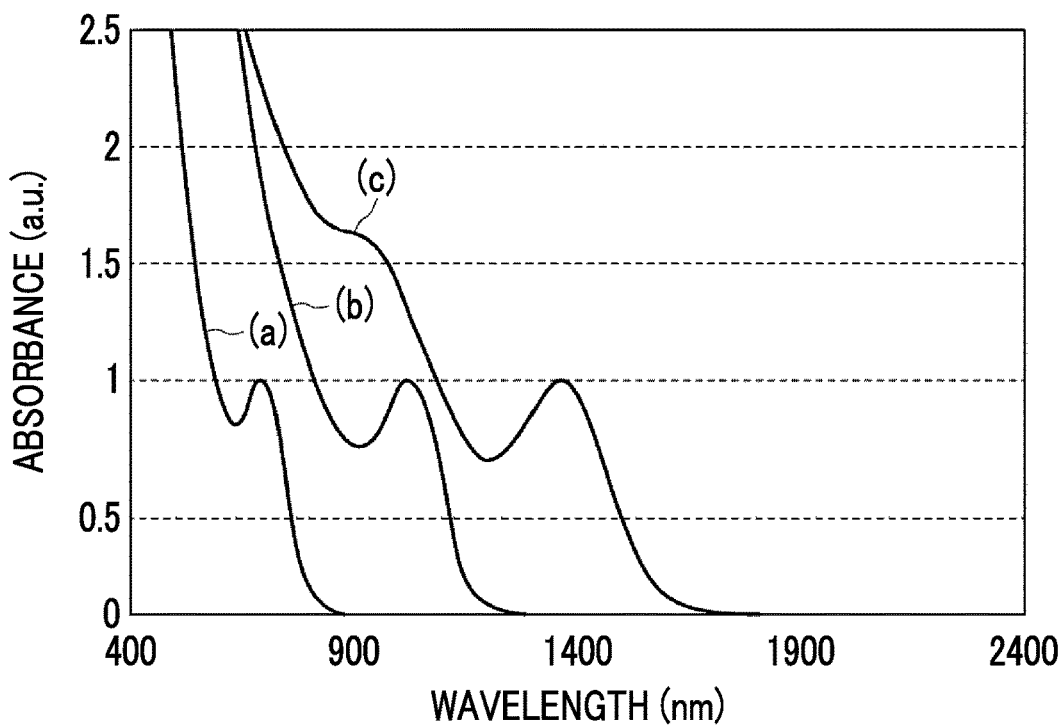
FIG. 4 is a graph illustrating the absorbance-wavelength characteristics of a phosphor.

FIG. 4 illustrates the absorbance-wavelength characteristics of the phosphor. The horizontal axis indicates a wavelength and the vertical axis indicates absorbance. FIG. 4 illustrates the absorbance-wavelength characteristics of three PbS-based phosphors (quantum dots) represented by graphs (a) to (c). As can be seen from FIG. 4, these phosphors have high absorbance in the wavelength range of about 400 nm to 500 nm. Therefore, it is preferable that a light source which emits light with a wavelength of 400 nm to 500 nm is used as the second light source 14.

Figure 5:
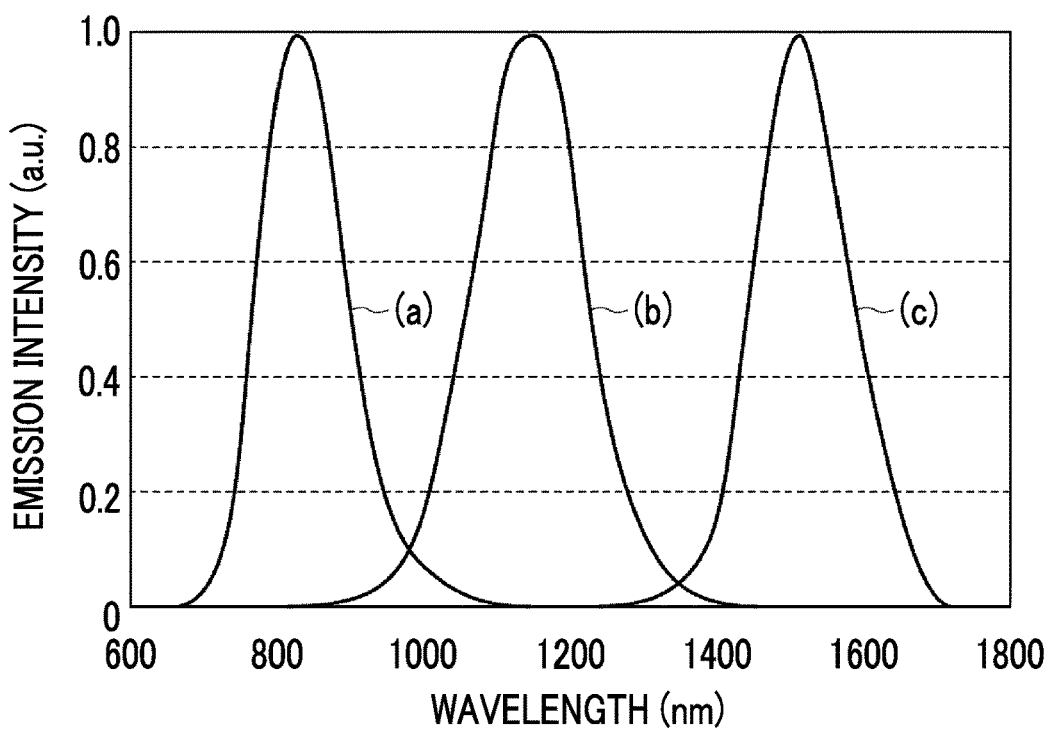
FIG. 5 is a graph illustrating the emission intensity-wavelength characteristics of the phosphor.

FIG. 5 illustrates the fluorescent emission intensity-wavelength characteristics of the phosphor. The horizontal axis indicates a wavelength and the vertical axis indicates emission intensity. FIG. 5 illustrates the emission intensity-wavelength characteristics of three PbS-based phosphors (quantum dots) represented by graphs (a) to (c). The phosphor represented by the graph (a) converts excitation light into fluorescent light with a wavelength of about 800 nm. The phosphor represented by the graph (b) converts excitation light into fluorescent light with a wavelength of about 1100 nm. The phosphor represented by the graph (c) converts excitation light into fluorescent light with a wavelength of about 1500 nm. It is possible to easily adjust the wavelengths of fluorescent light from the phosphors by changing the diameter of fluorescent particles. An appropriate particle diameter is selected according to the purpose of use and the light absorption/conversion member 51 is used to appropriately select the wavelength of light emitted to the subject while maintaining the wavelength of light emitted from the second light source 14. For example, the diameter of the fluorescent particle used in the graph (a) is 2.2 nm, the diameter of the fluorescent particle used in the graph (b) is 3.2 nm, and the diameter of the fluorescent particle used in the graph (c) is 5.3 nm. In addition, the phosphor may be a phosphor that can emit pulsed light in a nanosecond order. Alternatively, phosphors other than the quantum dot may be used. For example, a phosphor that is made of an organic fluorescent pigment and has a high response speed may be used.

Figure 6:
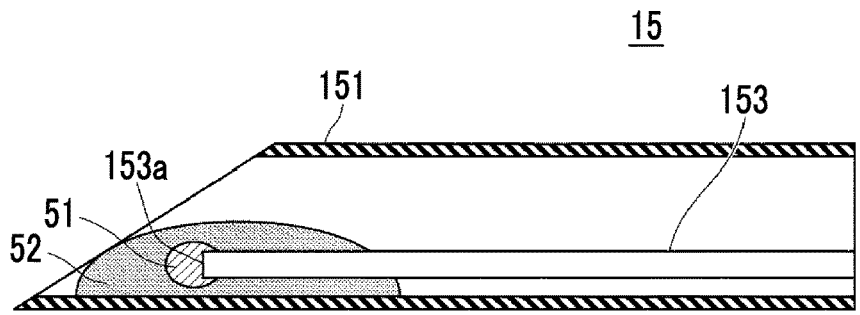
FIG. 6 is a cross-sectional view illustrating the vicinity of a leading end of a puncture needle according to a modification example.

The puncture needle 15 may include a transparent resin that transmits at least the light with the second wavelength. FIG. 6 is a cross-sectional view illustrating the leading end portion of the puncture needle 15 including the transparent resin. In FIG. 6, the optical fiber 154 which is a second light guide member is not illustrated. A transparent resin 52 transmits at least light with the third wavelength. The transparent resin 52 may transmit most of incident light with the third wavelength and does not need to transmit all of the incident light with the third wavelength. That is, the transparent resin 52 does not need to transmit 100% of the light with the third wavelength. For example, an epoxy resin (adhesive) is used as the transparent resin 52. For example, a thermosetting resin, an ultraviolet-curable resin, or a photocurable resin is used as the transparent resin 52.

A puncture needle main body 151 forming a main body portion of the puncture needle 15 has an inner cavity. The transparent resin 52 covers the light absorption/conversion member 51 in the inner cavity of the puncture needle main body 151. The transparent resin 52 may cover at least one of the optical fiber 153 or the optical fiber 154 (not illustrated) in the inner cavity of the puncture needle main body 151. The transparent resin 52 may function as a fixing member that fixes the light absorption/conversion member 51, the optical fiber 153, and the optical fiber 154 to the inner wall of the puncture needle main body 151. In FIG. 6, the light absorption/conversion member 51 covers the light emitting portion 153a of the optical fiber 153 and (the leading end portion of) the optical fiber 153 and the light absorption/conversion member 51 are fixed to the inner wall of the puncture needle main body 151 by the transparent resin 52. The light absorption/conversion member 51 also covers the light emitting portion 154a of the optical fiber 154 (not illustrated) and the optical fiber 154 is also fixed to the inner wall of the puncture needle main body 151 by the transparent resin 52.

In general, the biocompatibility of a wavelength conversion material, such as a phosphor, is not guaranteed. The light absorption/conversion member 51 including the wavelength conversion material covers the transparent resin 52 with biocompatibility, which makes it possible to prevent the inflow of the light absorption/conversion member 51 or a portion thereof (particularly, the wavelength conversion material) to a living body.

Returning to FIG. 1, the probe 11 includes, for example, a plurality of detector elements (ultrasound transducers) which are acoustic wave detection unit and are one-dimensionally arranged. After the puncture needle 15 is inserted into the subject, the probe 11 detects the photoacoustic waves (first photoacoustic waves) generated from the light absorption/conversion member 51 (see FIG. 2) and the photoacoustic waves (second photoacoustic waves) generated by the absorption of the light with the third wavelength emitted from the light absorption/conversion member 51 by the light absorber. The probe 11 performs the transmission of acoustic waves (ultrasonic waves) to the subject and the reception of the reflected acoustic waves (reflected ultrasonic waves) with respect to the transmitted ultrasonic waves, in addition to the detection of the photoacoustic waves. The transmission and reception of the sound waves may be performed at different positions. For example, ultrasonic waves may be transmitted from a position different from the position of the probe 11 and the probe 11 may receive the reflected ultrasonic waves with respect to the transmitted ultrasonic waves. The probe 11 is not limited to a linear probe and may be a convex probe or a sector probe.

The ultrasound unit 12 includes a receiving circuit 21, a receiving memory 22, data demultiplexing unit 23, photoacoustic image generation unit 24, ultrasound image generation unit 25, image output unit 26, a transmission control circuit 27, and control unit 28. The ultrasound unit 12 forms a signal processing device. The ultrasound unit 12 typically includes a processor, a memory, and a bus. A program related to the generation of a photoacoustic image is incorporated into the ultrasound unit 12. The program is executed to implement the functions of at least some of the components in the ultrasound unit 12.

The receiving circuit 21 receives a detection signal output from the probe 11 and stores the received detection signal in the receiving memory 22. The receiving circuit 21 typically includes a low noise amplifier, a variable gain amplifier, a low-pass filter, and an analog-to-digital convertor (AD convertor). The detection signal from the probe 11 is amplified by the low noise amplifier. The gain of the detection signal is adjusted by the variable gain amplifier according to a depth and a high-frequency component of the detection signal is cut by the low-pass filter. Then, the detection signal is converted into a digital signal by the AD convertor and is stored in the receiving memory 22. The receiving circuit 21 includes, for example, one integrated circuit (IC).

The probe 11 outputs a detection signal of the photoacoustic waves and a detection signal of the reflected ultrasonic waves. The AD-converted detection signals (sampling data) of the photoacoustic waves and the reflected ultrasonic waves are stored in the receiving memory 22. The data demultiplexing unit 23 reads out the sampling data of the detection signal of the photoacoustic waves from the receiving memory 22 and transmits the sampling data to the photoacoustic image generation unit 24. In addition, the data demultiplexing unit 23 reads out the sampling data of the reflected ultrasonic waves from the receiving memory 22 and transmits the sampling data to the ultrasound image generation unit (reflected acoustic image generation unit) 25.

The photoacoustic image generation unit 24 generates a photoacoustic image on the basis of the detection signal of the photoacoustic waves detected by the probe 11. The generation of the photoacoustic image includes, for example, image reconfiguration, such as phasing addition, detection, and logarithmic conversion. The ultrasound image generation unit 25 generates an ultrasound image (reflected acoustic image) on the basis of the detection signal of the reflected ultrasonic waves detected by the probe 11. The generation of the ultrasound image includes, for example, image reconfiguration, such as phasing addition, detection, and logarithmic conversion. The image output unit 26 outputs the photoacoustic image and the ultrasound image to image display unit 16 such as a display device.

The control unit 28 controls each component in the ultrasound unit 12. For example, in a case in which a photoacoustic image is acquired, the control unit 28 transmits a trigger signal to the first light source 13 or the second light source 14 such that the first light source 13 or the second light source 14 emits laser light. In addition, the control unit 28 transmits a sampling trigger signal to the receiving circuit 21 to control, for example, the sampling start time of the photoacoustic waves with the emission of the laser light.

In a case in which an ultrasound image is acquired, the control unit 28 transmits an ultrasound transmission trigger signal for instructing the transmission of ultrasonic waves to the transmission control circuit 27. In a case in which the ultrasound transmission trigger signal is received, the transmission control circuit 27 directs the probe 11 to transmit ultrasonic waves. For example, the probe 11 performs scanning while shifting acoustic lines one by one to detect reflected ultrasonic waves. The control unit 28 transmits a sampling trigger signal to the receiving circuit 21 in synchronization with the transmission of the ultrasonic waves to start the sampling of the reflected ultrasonic waves.

The control unit 28 may switch the operation mode of the photoacoustic image generation apparatus 10 among four operation modes. In a first operation mode, the first light source 13 emits light with the first wavelength, the photoacoustic waves (first photoacoustic waves) generated from the light absorption/conversion member 51 are detected, and a photoacoustic image (first photoacoustic image) is generated. In a second operation mode, the second light source 14 emits light with the second wavelength, the light absorption/conversion member 51 converts the light with the second wavelength into light with the third wavelength, the photoacoustic waves (second photoacoustic waves) generated by the irradiation of the subject with the light with the third wavelength are detected, and a photoacoustic image (second photoacoustic image) is generated. In a third operation mode, the first light source 13 emits light with the first wavelength, the second light source 14 emits light with the second wavelength, both the photoacoustic waves (first photoacoustic waves) generated from the light absorption/conversion member 51 and the photoacoustic waves (second photoacoustic waves) generated by the irradiation of the subject with the light with the third wavelength converted by the light absorption/conversion member 51 are detected, and a photoacoustic image (third photoacoustic image) is generated. In a fourth operation mode, ultrasonic waves are transmitted to the subject, ultrasonic waves reflected from the subject are detected, and an ultrasound image is generated. A user, such as a doctor, can select the operation mode using input means (not illustrated), such as a keyboard or a console switch. Alternatively, arbitrary operation modes among the four operation modes may be sequentially automatically switched and images obtained in each operation mode may be combined and displayed.

Figure 7:
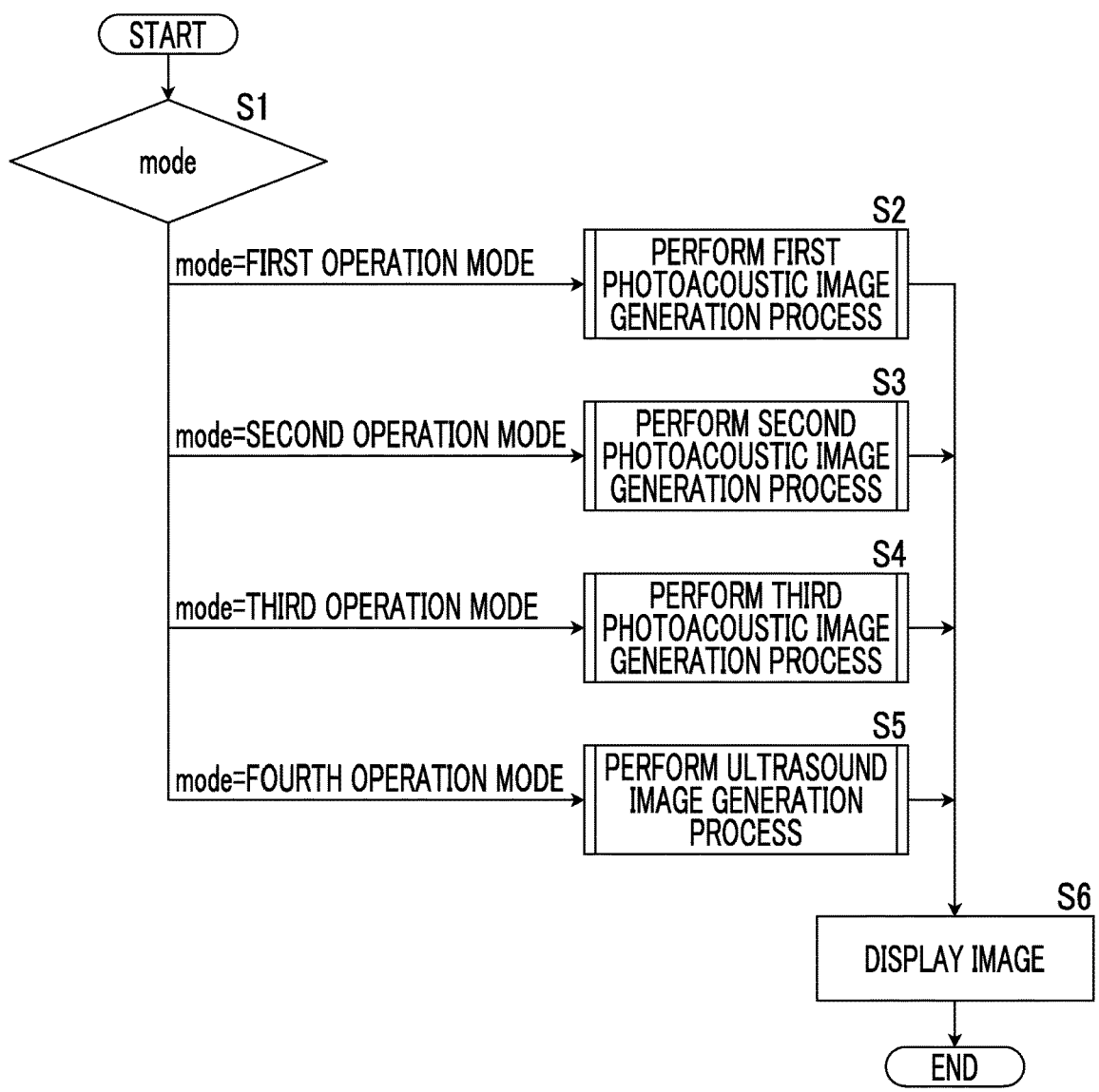
FIG. 7 is a flowchart illustrating the procedure of an operation of the photoacoustic image generation apparatus.

Next, the procedure of an operation will be described. FIG. 7 illustrates the procedure of the operation of the photoacoustic image generation apparatus 10. The operation mode selected by the user is stored in a variable mode. The control unit 28 switches a process according to the variable mode (Step S1). In a case in which the variable mode is the first operation mode, the control unit 28 performs a first photoacoustic image generation process in the photoacoustic image generation apparatus 10 (Step S2). In a case in which the variable mode is the second operation mode, the control unit 28 performs a second photoacoustic image generation process in the photoacoustic image generation apparatus 10 (Step S3). In a case in which the variable mode is the third operation mode, the control unit 28 performs a third photoacoustic image generation process in the photoacoustic image generation apparatus 10 (Step S4). In a case in which the variable mode is the fourth operation mode, the control unit 28 performs an ultrasound image generation process in the photoacoustic image generation apparatus 10 (Step S5). The photoacoustic image generation apparatus 10 displays the image generated in Step S2, Step S3, Step S4, or Step S5 on the image display unit 16 (Step S6).

Figure 8:
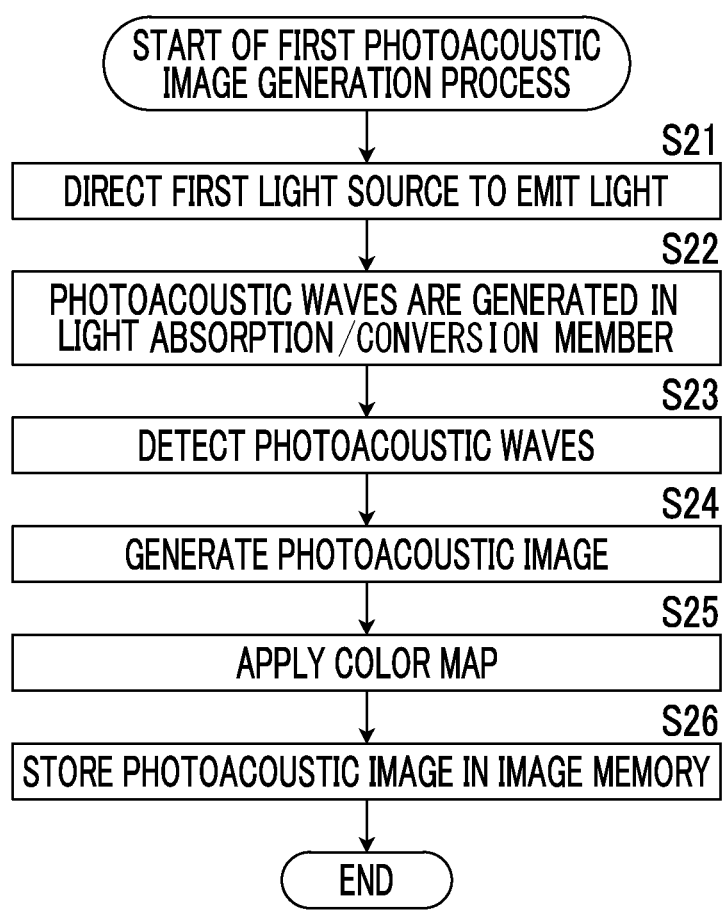
FIG. 8 is a flowchart illustrating the procedure of a first photoacoustic image generation process.

FIG. 8 illustrates the procedure of the first photoacoustic image generation process. The control unit 28 directs the first light source 13 to emit light (Step S21). In Step S21, the control unit 28 transmits a trigger signal to the first light source 13. In a case in which the first light source 13 is a solid-state laser device including a flash lamp and a Q-switch, the trigger signal includes, for example, a flash lamp trigger signal and a Q-switch trigger signal. In the first light source 13, the flash lamp is turned on in response to the flash lamp trigger signal and then the Q-switch is driven in response to the Q-switch trigger signal to emit pulsed laser light with the first wavelength. In a case in which the first light source 13 is a laser diode, a laser driver circuit makes a predetermined amount of current flow to the laser diode for the time corresponding to a pulse width in response to the trigger signal to emit pulsed laser light with the first wavelength.

The pulsed laser light emitted from the first light source 13 is incident on the optical fiber 153 through the optical fiber 17 and the optical connector 19, is guided to the vicinity of the leading end of the puncture needle 15 by the optical fiber 153, and is emitted from the first light emitting portion 153a (see FIG. 2). At least a portion of the pulsed laser light is emitted to the light absorption/conversion member 51 provided at the leading end of the puncture needle 15. The light absorber included in the light absorption/conversion member 51 absorbs the light with the first wavelength and generates photoacoustic waves (Step S22).

The probe 11 detects the photoacoustic waves generated by the emission of the pulsed laser light, that is, the photoacoustic waves (first photoacoustic waves) generated from the light absorption/conversion member 51 (Step S23). The photoacoustic waves detected by the probe are received by the receiving circuit 21 and the sampling data of the photoacoustic waves is stored in the receiving memory 22. The photoacoustic image generation unit 24 receives the sampling data of the detection signal of the photoacoustic waves through the data demultiplexing unit 23 and generates a photoacoustic image (first photoacoustic image) (Step S24). The photoacoustic image generation unit 24 may apply a color map (Step S25) to convert the signal intensity of the photoacoustic image into a color. The photoacoustic image generated by the photoacoustic image generation unit 24 is stored in, for example, an image memory (not illustrated) of the image output unit 26 (Step S26).

Figure 9:
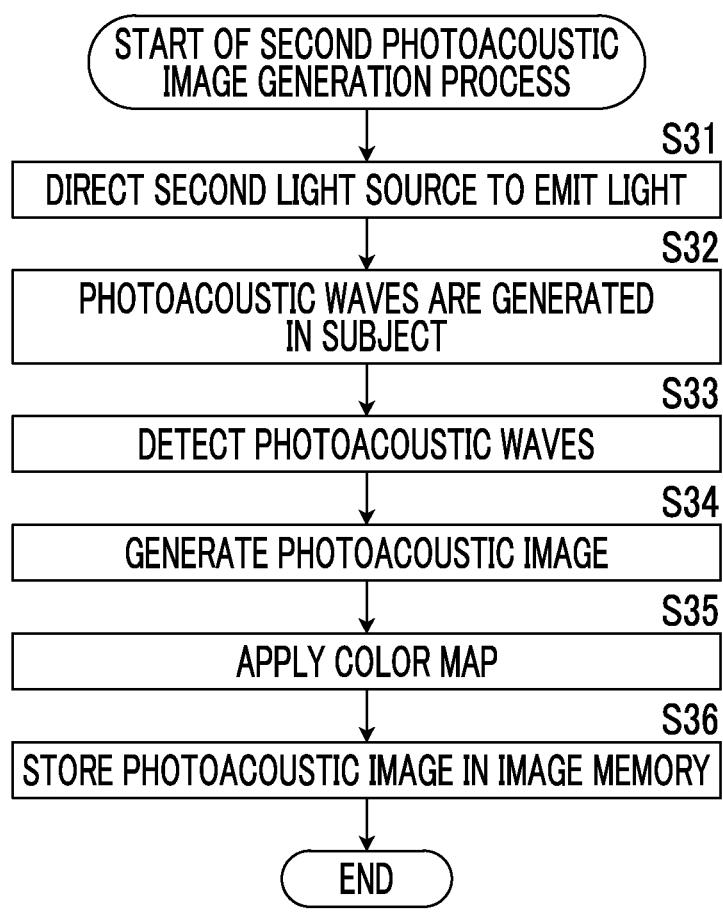
FIG. 9 is a flowchart illustrating the procedure of a second photoacoustic image generation process.

FIG. 9 illustrates the procedure of the second photoacoustic image generation process. The control unit 28 directs the second light source 14 to emit light (Step S31). In Step S31, the control unit 28 transmits a trigger signal to the second light source 14. In a case in which the second light source 14 is a solid-state laser device including a flash lamp and a Q-switch, the trigger signal includes, for example, a flash lamp trigger signal and a Q-switch trigger signal. In the second light source 14, the flash lamp is turned on in response to the flash lamp trigger signal and then the Q-switch is driven in response to the Q-switch trigger signal to emit pulsed laser light with the second wavelength. In a case in which the second light source 14 is a laser diode, a laser driver circuit makes a predetermined amount of current flow to the laser diode for the time corresponding to a pulse width in response to the trigger signal to emit pulsed laser light with the first wavelength.

The pulsed laser light emitted from the second light source 14 is incident on the optical fiber 154 through the optical fiber 18 and the optical connector 20, is guided to the vicinity of the leading end of the puncture needle 15 by the optical fiber 154, and is emitted from the second light emitting portion 154a (see FIG. 2). At least a portion of the pulsed laser light is emitted to the light absorption/conversion member 51 provided at the leading end of the puncture needle 15. The phosphor included in the light absorption/conversion member 51 converts the light with the second wavelength into light with the third wavelength. The converted light with the third wavelength is emitted from the opening of the puncture needle 15 into the subject. In a case in which an absorber that absorbs the light with the third wavelength is present in the emission range of the light with the third wavelength, photoacoustic waves (second photoacoustic waves) are generated from the absorber (Step S32).

The probe 11 detects the photoacoustic waves generated by the emission of the light with the third wavelength, that is, the photoacoustic waves (second photoacoustic waves) generated from the subject (Step S33). The photoacoustic waves detected by the probe are received by the receiving circuit 21 and the sampling data of the photoacoustic waves is stored in the receiving memory 22. The photoacoustic image generation unit 24 receives the sampling data of the detection signal of the photoacoustic waves through the data demultiplexing unit 23 and generates a photoacoustic image (second photoacoustic image) (Step S34). The photoacoustic image generation unit 24 may apply a color map (Step S35) to convert the signal intensity of the photoacoustic image into a color. It is preferable that the color map used in Step S35 is different from the color map used to generate the first photoacoustic image. The photoacoustic image generated by the photoacoustic image generation unit 24 is stored in, for example, the image memory (not illustrated) of the image output unit 26 (Step S36).

Figure 10:
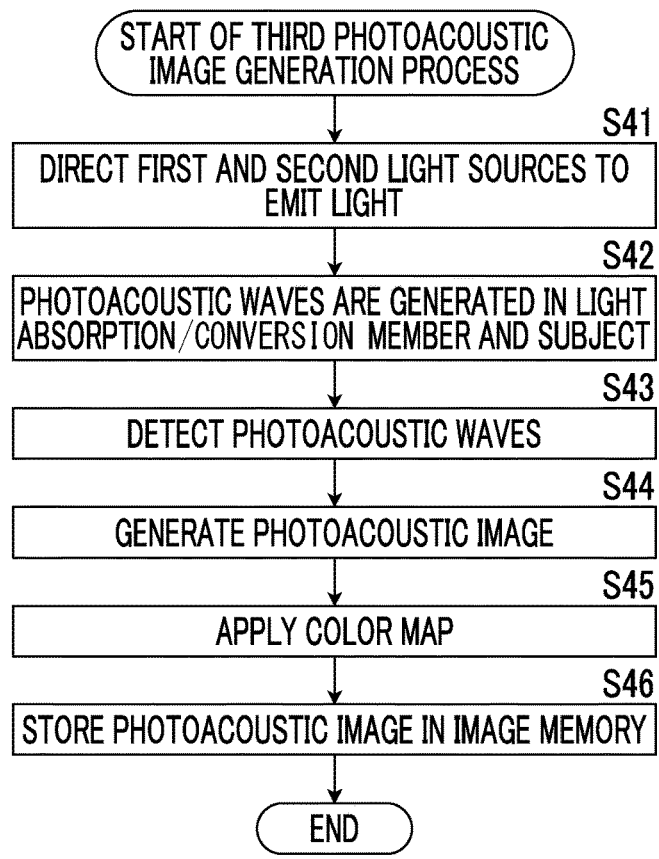
FIG. 10 is a flowchart illustrating the procedure of a third photoacoustic image generation process.

FIG. 10 illustrates the procedure of the third photoacoustic image generation process. The control unit 28 directs the first light source 13 and the second light source 14 to emit light (Step S41). The emission of light from the first light source 13 by the control unit 28 is performed in the same procedure as that in Step S21 of FIG. 8. The emission of light from the second light source 14 is performed in the same procedure as that in Step S31 of FIG. 9.

The pulsed laser light emitted from the first light source 13 is incident on the optical fiber 153 through the optical fiber 17 and the optical connector 19, is guided to the vicinity of the leading end of the puncture needle 15 by the optical fiber 153, and is emitted from the first light emitting portion 153a (see FIG. 2). At least a portion of the pulsed laser light is emitted to the light absorption/conversion member 51 provided at the leading end of the puncture needle 15. In addition, the pulsed laser light emitted from the second light source 14 is incident on the optical fiber 154 through the optical fiber 18 and the optical connector 20, is guided to the vicinity of the leading end of the puncture needle 15 by the optical fiber 154, and is emitted from the second light emitting portion 154a (see FIG. 2). At least a portion of the pulsed laser light is emitted to the light absorption/conversion member 51. The phosphor included in the light absorption/conversion member 51 converts the emitted light with the second wavelength into light with the third wavelength. The converted light with the third wavelength is emitted from the opening of the puncture needle 15 into the subject. The light absorber included in the light absorption/conversion member 51 absorbs the light with the first wavelength and generates photoacoustic waves (first photoacoustic waves). The absorber that is present in the emission range of the light with the third wavelength absorbs the light with the third wavelength and generates photoacoustic waves (Step S42).

The probe 11 detects the photoacoustic waves generated by the emission of the laser light, that is, the first photoacoustic waves generated from the light absorption/conversion member 51 and the second photoacoustic waves generated from the absorber in the subject (Step S43). The photoacoustic waves detected by the probe are received by the receiving circuit 21 and the sampling data of the photoacoustic waves is stored in the receiving memory 22. The photoacoustic image generation unit 24 receives the sampling data of the detection signal of the photoacoustic waves through the data demultiplexing unit 23 and generates a photoacoustic image (third photoacoustic image) (Step S44). The photoacoustic image generation unit 24 may apply a color map (Step S45) to convert the signal intensity of the photoacoustic image into a color. The photoacoustic image generated by the photoacoustic image generation unit 24 is stored in, for example, the image memory (not illustrated) of the image output unit 26 (Step S46).

Figure 11:
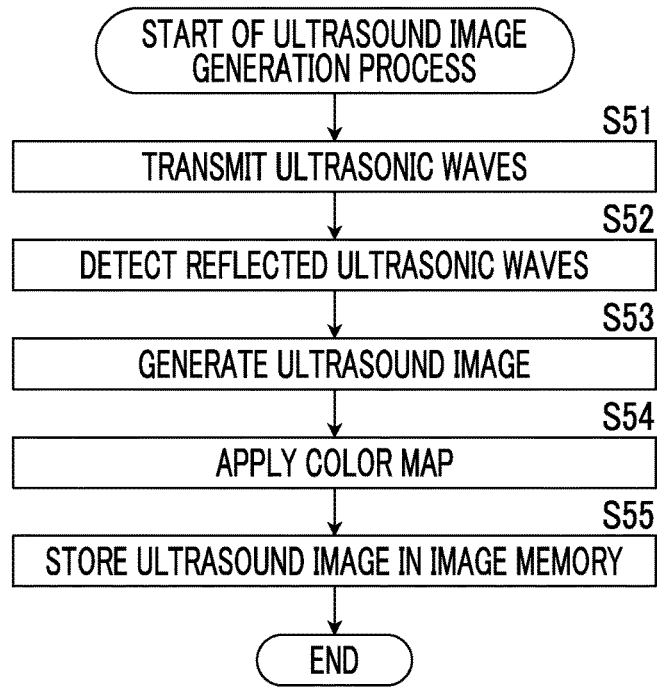
FIG. 11 is a flowchart illustrating the procedure of an ultrasound image generation process.

FIG. 11 illustrates the procedure of the ultrasound image generation process. The control unit 28 transmits an ultrasound trigger signal to the transmission control circuit 27. The transmission control circuit 27 directs the probe 11 to transmit ultrasonic waves in response to the ultrasound trigger signal (Step S51). The probe 11 transmits ultrasonic waves and detects reflected ultrasonic waves (Step S52). The reflected ultrasonic waves detected by the probe 11 are received by the receiving circuit 21 and the sampling data of the reflected ultrasonic waves is stored in the receiving memory 22. The ultrasound image generation unit 25 receives the sampling data of the detection signal of the reflected ultrasonic waves through the data demultiplexing unit 23 and generates an ultrasound image (Step S53). The ultrasound image generation unit 25 may apply a color map (Step S54) to convert the signal intensity of the ultrasound image into a color. The ultrasound image generated by the ultrasound image generation unit 25 is stored in, for example, the image memory (not illustrated) of the image output unit 26 (Step S55).

The user can appropriately switch the operation mode among the first to fourth operation modes while inserting the puncture needle 15. For example, when starting the insertion of the puncture needle 15, the user selects the fourth operation mode and performs an operation such that an ultrasound image is displayed on the image display unit 16. After starting the insertion, the user switches the operation mode to the first operation mode and performs an operation such that the first photoacoustic image is displayed on the image display unit 16. In the first photoacoustic image, the position of the light absorption/conversion member 51 that absorbs light with the first wavelength and generates photoacoustic waves appears as a bright point. Therefore, it is possible to check the position of the leading end of the puncture needle 15 with reference to the first photoacoustic image.

In a case in which the puncture needle 15 is inserted to a certain depth, the user switches the operation mode to the second operation mode and performs an operation such that the second photoacoustic image is displayed on the image display unit 16. In a case in which a light absorber that absorbs light with the third wavelength is present in the vicinity of the leading end of the puncture needle 15 in the subject, the position of the light absorber appears as a bright point in the second photoacoustic image. For example, in a case in which the third wavelength is a wavelength absorbed by blood and blood is present in the vicinity of the leading end of the puncture needle 15, a bright point appears in the second photoacoustic image. The user can determine whether the puncture needle 15 has been inserted to the part in which blood is present, on the basis of whether a bright point is present. The photoacoustic image generation apparatus 10 may determine whether the sum of the signals of the second photoacoustic image is equal to or greater than a threshold value. In a case in which the sum of the signals is equal to or greater than the threshold value, the photoacoustic image generation apparatus 10 may notify the user of the determination result. The user may perform a needling operation while alternately switching the operation mode between the first operation mode and the second operation mode or after selecting the third operation mode.

In the above description, the first photoacoustic image, the second photoacoustic image, the third photoacoustic image, and the ultrasound image are generated in the independent operation modes. However, the present disclosure is not limited thereto. For example, at least one of the first photoacoustic image, the second photoacoustic image, or the third photoacoustic image and the ultrasound image may be generated in one operation mode. In this case, the image output unit 26 may function as image combination unit for combining at least two of the first photoacoustic image, the second photoacoustic image, the third photoacoustic image, and the ultrasound image. For example, the image output unit 26 may combine the first photoacoustic image and the ultrasound image and display a composite image on the image display unit 16. Alternatively, the image output unit 26 may combine the second photoacoustic image and the ultrasound image and display a composite image on the image display unit 16. The image output unit 26 may combine the third photoacoustic image and the ultrasound image and display a composite image on the image display unit 16. In addition, the image output unit 26 may combine the first photoacoustic image, the second photoacoustic image, and the ultrasound image and display a composite image on the image display unit 16.

In this embodiment, the light with the first wavelength emitted from the first light source 13 is emitted to the light absorption/conversion member 51 through the optical fiber 17 and the optical fiber 153 and the light with the second wavelength emitted from the second light source 14 is emitted to the light absorption/conversion member 51 through the optical fiber 18 and the optical fiber 154. In a case in which the light absorption/conversion member 51 is irradiated with the light with the first wavelength, the light absorption/conversion member 51 generates photoacoustic waves and the first photoacoustic image is generated on the basis of the detection signal of the photoacoustic waves. The first photoacoustic image includes the positional information of the leading end of the puncture needle 15. In contrast, in a case in which the light absorption/conversion member 51 is irradiated with the light with the second wavelength, the light absorption/conversion member 51 converts the light with the second wavelength into light with the third wavelength. The light with the third wavelength is emitted from the leading end of the puncture needle 15 to the subject. In a case in which a light absorber is present in the part irradiated with the light with the third wavelength in the subject, photoacoustic waves are generated from the light absorber and the second photoacoustic image is generated on the basis of the detection signal of the photoacoustic waves. The second photoacoustic image includes surrounding environment information.

In this embodiment, the light absorption/conversion member 51 is selectively irradiated with the light with the first wavelength and the light with the second wavelength. Therefore, it is possible to separately acquire both the positional information and the surrounding environment information of the tip of the needle, using one puncture needle 15. In this embodiment, in the puncture needle 15, the optical fiber 153 is used to guide light with the first wavelength and the optical fiber 154 is used to guide light with the second wavelength. Since the light with the first wavelength and the light with the second wavelength are guided by the individual optical fibers, it is possible to irradiate the light absorption/conversion member 51 with the light with the first wavelength and the light with the second wavelength at the same time. In this case, it is possible to acquire the positional information and the surrounding environment information of the tip of the needle at the same time.

In this embodiment, the phosphor used for the light absorption/conversion member 51 is changed to change the wavelength of fluorescent light. For example, a plurality of puncture needles 15 are prepared and the phosphors included in the light absorption/conversion members 51 in the puncture needles 15 are different from each other. In this case, the wavelength (third wavelength) of light to be converted is appropriately selected according to an evaluation target material. With this configuration, it is possible to change the wavelength of light emitted to the subject only by changing the puncture needle 15 used, without changing the wavelength of light emitted from the second light source 14. Therefore, even in a case in which a plurality of light sources emitting light components with a plurality of wavelengths are not prepared, it is possible to evaluate whether a plurality of materials with different absorption wavelengths are present in the vicinity of the puncture needle and to reduce the overall cost of the apparatus.

Next, a second embodiment of the present disclosure will be described. This embodiment differs from the first embodiment in that the puncture needle 15 includes an outer needle and an inner needle. The other configurations may be the same as those in the first embodiment.

Figure 12:
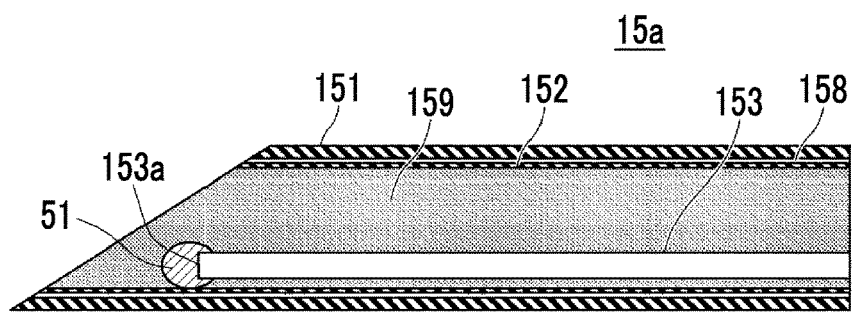
FIG. 12 is a cross-sectional view illustrating the vicinity of a leading end of a puncture needle according to a second embodiment.

FIG. 12 is a cross-sectional view illustrating a puncture needle 15a according to this embodiment. In FIG. 12, the optical fiber 154 (see FIG. 2) is not illustrated. A puncture needle main body 151 forming the outer needle has an opening at an acute leading end and has an inner cavity. An inner needle 152 has substantially the same outside diameter as the inner cavity of the puncture needle main body 151 and is configured so as to be inserted into or removed from the hollow puncture needle main body 151. The inner needle 152 is inserted into the inner cavity of the puncture needle main body 151 from the base end side of the puncture needle main body 151 to seal at least a portion of the inner cavity of the puncture needle main body 151 to the extent that, for example, a section of the living body is prevented from being inserted into the inner cavity. A protruding portion for connection position adjustment is provided in a base end portion of the inner needle 152. A groove into which the protruding portion provided in the base end portion of the inner needle 152 is fitted is provided in a base end portion of the puncture needle main body 151. In a case in which the inner needle 152 is set in the puncture needle main body 151, the protruding portion provided in the base end portion of the inner needle 152 and the groove provided in the base end portion of the puncture needle main body 151 are positioned and the base end portion of the inner needle 152 is fitted to the base end portion of the puncture needle main body 151.

The inner needle 152 includes the optical fiber 153, the optical fiber 154 (not illustrated in FIG. 12), the light absorption/conversion member 51, a tube 158, and a transparent resin 159. The tube 158 is, for example, a hollow tube made of polyimide. The tube 158 may be a metal tube made of, for example, stainless steel. The outside diameter of the tube 158 is slightly less than the diameter of the inner cavity of the puncture needle main body 151. The transparent resin 159 is provided in the tube 158. For example, an epoxy resin (adhesive) is used as the transparent resin 159. The tube 158 and the transparent resin 159 are acute, similarly to the acute leading end of the puncture needle. A photocurable resin, a thermosetting resin, or a room-temperature-curable resin may be used as the transparent resin 159.

The optical fiber 153 and the optical fiber 154 are covered with the transparent resin 159 in the tube 158. The light absorption/conversion member 51 is provided at the leading ends of the optical fiber 153 and the optical fiber 154. The light absorption/conversion member 51 is irradiated with light emitted from the first light emitting portion 153a and the second light emitting portion 154a. In a case in which the first light source 13 (see FIG. 1) emits light, the light absorption/conversion member 51 absorbs the emitted light with the first wavelength and photoacoustic waves are generated at the leading end of the puncture needle. In a case in which the second light source 14 emits light, the light absorption/conversion member 51 converts the emitted light with the second wavelength into light with the third wavelength and the light with the third wavelength is emitted to the subject.

An operator, such as a doctor, inserts the puncture needle 15a into the subject, with the inner needle 152 set in the puncture needle main body 151. Since the inner cavity of the puncture needle main body 151 is closed by the inner needle 152, it is possible to prevent a piece of flesh from getting into the needle while the needle is being inserted and thus to prevent the needling sense of the operator from being hindered. In addition, it is possible to prevent the inflow of water from the part to be needled to the inner cavity of the puncture needle main body 151. After inserting the needle into the subject, the operator releases the connection between the base end portion of the inner needle 152 and the base end portion of the puncture needle main body 151 and takes the inner needle 152 out of the puncture needle main body 151. After taking the inner needle 152 out of the puncture needle main body 151. the operator can attach, for example, a syringe to the base end portion of the puncture needle main body 151 and inject a medicine such as an anesthetic.

Figure 13:
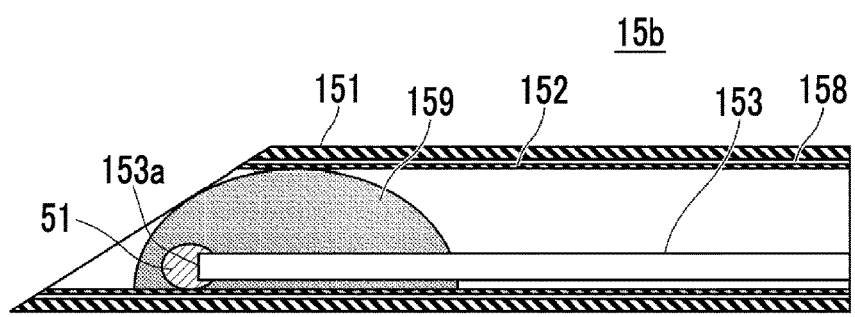
FIG. 13 is a cross-sectional view illustrating the vicinity of a leading end of a puncture needle according to a modification example.

In addition, the transparent resin 159 may close at least a leading end portion of the tube 158 and does not necessarily close the entire inside of the tube 158. FIG. 13 is a cross-sectional view illustrating the vicinity of the leading end of a puncture needle according to a modification example. In a puncture needle 15b, a transparent resin 159 covers the light absorption/conversion member 51 covering the light emitting portion 153a of the optical fiber 153 and the light emitting portion 154a of the optical fiber 154 (not illustrated in FIG. 13) and (the leading end portions of) the optical fibers 153 and 154 and the light absorption/conversion member 51 are fixed to the inner wall of the tube 158 by the transparent resin 159. In addition, the transparent resin 159 closes an opening provided in the leading end portion of the tube 158. In a case in which this configuration is used, it is possible to prevent the inflow of, for example, water into the inner needle 152.

The optical fiber 153 and the optical fiber 154 do not need to be fixed to the inner wall of the tube 158 by the transparent resin 159 and may be fixed to the inner cavity of the tube 158 by the light absorption/conversion member 51. The leading end portion of the tube 158 may be closed by the light absorption/conversion member 51. In this case, the transparent resin 159 may be omitted.

In this embodiment, the puncture needle 15a includes the inner needle 152 provided in the inner cavity of the puncture needle main body 151. The inner needle 152 closes the inner cavity of the puncture needle main body 151 while the puncture needle 15a is being inserted. Therefore, it is possible to prevent the needling sense of the operator from being hindered and to prevent the inflow of water from the part to be needled to the inner cavity of the puncture needle main body 151. The other effects are the same as those in the first embodiment or the second embodiment.

In each of the above-described embodiments, the puncture needle 15 is considered as an insert. However, the present disclosure is not limited thereto. The insert may be a radio frequency ablation needle including an electrode that is used for radio frequency ablation, a catheter that is inserted into a blood vessel, or a guide wire for a catheter that is inserted into a blood vessel. Alternatively, the insert may be an optical fiber for laser treatment.

In each of the above-described embodiments, a needle having an opening at the leading end is assumed as the needle. However, the opening is not necessarily provided at the leading end of the needle. The needle is not limited to an injection needle and may be a biopsy needle used for biopsy. That is, the needle may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen.

The puncture needle 15 is not limited to the needle that is inserted from the outside of the subject into the subject through the skin and may be a needle for ultrasound endoscopy. The optical fibers 153 and 154 and the light absorption/conversion member 51 may be provided in the needle for ultrasound endoscopy. The light absorption/conversion member 51 provided in the leading end portion of the needle may be irradiated with at least one of light with the first wavelength or light with the second wavelength. Then, photoacoustic waves may be detected and a photoacoustic image (the first photoacoustic image, the second photoacoustic image, or the third photoacoustic image) may be generated. In this case, it is possible to perform needling while observing the first photoacoustic image and checking the position of the leading end portion of the needle for ultrasound endoscopy. In addition, it is possible to determine whether an evaluation target material is present in the vicinity of the needle, using the second photoacoustic image. In a case in which the third photoacoustic image is generated, it is possible to determine the position of the tip of the needle and to determine whether an evaluation target material is present. The first photoacoustic waves generated from the leading end portion of the needle for ultrasound endoscopy and the second photoacoustic waves generated from the vicinity of the leading end portion may be detected by a probe for body surface or a probe that is incorporated into an endoscope.

Figure 14:
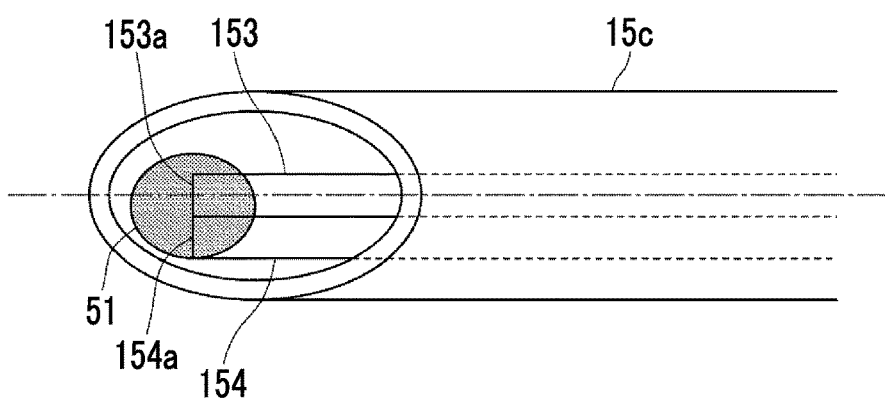
FIG. 14 is a cross-sectional view illustrating a puncture needle according to another modification example.

The optical fiber 153 and the optical fiber 154 in the puncture needle 15 have any positional relationship therebetween. FIG. 14 illustrates a puncture needle according to another modification example. In this modification example, similarly to the puncture needle illustrated in FIG. 2, the optical fiber 153 and the optical fiber 154 are arranged side by side in a puncture needle 15c. In FIG. 14, particularly, of two optical fibers, the optical fiber 153 that guides light with the first wavelength is disposed at the center of a puncture needle 15c in a width direction. Here, the position of the center of the puncture needle in the width direction means the position of the center in the width direction in a case in which the needle is viewed from the upper side with a sharp portion of the leading end of the needle facing down or up. As illustrated in FIG. 14, in a case in which the first light emitting portion 153a provided at the leading end of the optical fiber 153 is disposed at the center of (the opening of) the puncture needle 15 in the width direction, it is possible to generate the first photoacoustic waves at the center of the puncture needle 15c in the width direction.

Figure 15:
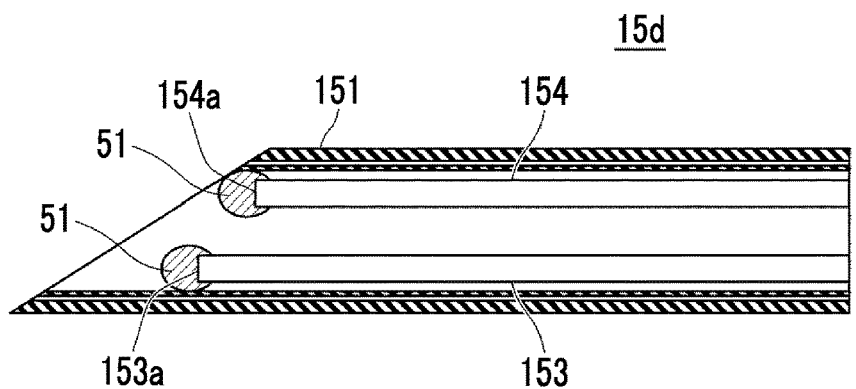
FIG. 15 is a cross-sectional view illustrating a puncture needle according to still another modification example.

The optical fiber 153 and the optical fiber 154 are not necessarily arranged in the width direction of the puncture needle. FIG. 15 illustrates a puncture needle according to yet another modification example. In a puncture needle 15d according to this modification example, the optical fiber 153 is provided on an inner wall on the side where the puncture needle main body 151 is the longest and the leading end is sharp. In contrast, the optical fiber 154 is provided on an inner wall (a position that is rotated 180° about the axial direction of the puncture needle) opposite to the inner wall. In this modification example, the first light emitting portion 153a provided at the leading end of the optical fiber 153 and the second light emitting portion 154a provided at the leading end of the optical fiber 154 are separated from each other. In this case, the first light emitting portion 153a and the second light emitting portion 154a do not need to be covered by one light absorption/conversion member 51. In addition, the first light emitting portion 153a and the second light emitting portion 154a do not need to be covered by the same member. For example, the first light emitting portion 153a may be covered by a resin that includes the light absorber and does not include the phosphor described in the first embodiment and the second light emitting portion 154a may be covered by a resin that includes the phosphor and does not include the light absorber described in the first embodiment.

The present disclosure has been described above on the basis of the preferred embodiments. However, the photoacoustic image generation apparatus and the insert according to the present disclosure are not limited to the above-described embodiments. Various modifications and changes of the configurations according to the above-described embodiments are also included in the scope of the present disclosure.

What is claimed is:

1. An insert that is at least partially inserted into a subject, comprising:
   a first light guide member that guides light with a first wavelength;
   a first light emitting portion from which the light guided by the first light guide member is emitted;
   a second light guide member that is provided so as to be adjacent to the first light guide member and guides light with a second wavelength different from the first wavelength;
   a second light emitting portion from which the light guided by the second light guide member is emitted;
   a light absorption/conversion member that at least partially covers light emission surfaces of the first light emitting portion and the second light emitting portion, absorbs the light with the first wavelength emitted from the first light emitting portion to generate photoacoustic waves, and converts the light with the second wavelength emitted from the second light emitting portion into light with a third wavelength different from the first wavelength and the second wavelength; and
   a transparent resin that transmits the light with the third wavelength,
   wherein
      the light absorption/conversion member is covered with the transparent resin,
      the insert has an inner cavity, and
      the first light guide member, the second light guide member, and the light absorption/conversion member are fixed to an inner wall of the inner cavity by the transparent resin.

2. The insert according to claim 1,
wherein the light absorption/conversion member includes a light absorber that transmits the light with the second wavelength and the light with the third wavelength and absorbs the light with the first wavelength to generate photoacoustic waves, a phosphor that absorbs the light with the second wavelength and converts the light with the second wavelength into the light with the third wavelength, and a resin including the light absorber and the phosphor.

3. The insert according to claim 1,
wherein
the light absorption/conversion member functions as a fixing member that fixes the first light guide member and the second light guide member to an inner wall of the inner cavity.

4. The insert according to claim 1,
wherein the first light emitting portion is provided at a center of the insert in a width direction.

5. A photoacoustic image generation apparatus comprising:
   a first light source that emits light with a first wavelength;
   a second light source that emits light with a second wavelength different from the first wavelength;
   an insert that is at least partially inserted into a subject and includes a first light guide member that guides the light with the first wavelength, a first light emitting portion from which the light guided by the first light guide member is emitted, a second light guide member that is provided so as to be adjacent to the first light guide member and guides the light with the second wavelength, a second light emitting portion from which the light guided by the second light guide member is emitted, and a light absorption/conversion member that at least partially covers light emission surfaces of the first light emitting portion and the second light emitting portion, absorbs the light with the first wavelength emitted from the first light emitting portion to generate first photoacoustic waves, and converts the light with the second wavelength emitted from the second light emitting portion into light with a third wavelength different from the first wavelength and the second wavelength;

acoustic wave detection unit that detects the first photoacoustic waves and second photoacoustic waves which are generated in the subject by the emission of the light with the third wavelength to the subject; and photoacoustic image generation unit that generates a first photoacoustic image on the basis of the first photoacoustic waves, and generates a second photoacoustic image on the basis of the second photoacoustic waves.

6. The photoacoustic image generation apparatus according to claim 5, wherein the acoustic wave detection unit further detects reflected acoustic waves with respect to acoustic waves transmitted to the subject, and the photoacoustic image generation apparatus further comprises reflected acoustic image generation unit that generates a reflected acoustic image on the basis of the reflected acoustic waves.

7. An insert that is at least partially inserted into a subject, comprising:

a first light guide member that guides light with a first wavelength;

a first light emitting portion from which the light guided by the first light guide member is emitted;

a second light guide member that is provided so as to be adjacent to the first light guide member and guides light with a second wavelength different from the first wavelength;

a second light emitting portion from which the light guided by the second light guide member is emitted; and a light absorption/conversion member that at least partially covers light emission surfaces of the first light emitting portion and the second light emitting portion, absorbs the light with the first wavelength emitted from the first light emitting portion to generate photoacoustic waves, and converts the light with the second wavelength emitted from the second light emitting portion into light with a third wavelength different from the first wavelength and the second wavelength, wherein the insert is a puncture needle having an inner cavity, the insert further includes a hollow tube in which the first light guide member and the second light guide member are accommodated, the puncture needle includes an inner needle and an outer needle, the inner needle includes the hollow tube, and the inner needle seals at least a portion of the inner cavity.

8. An insert that is at least partially inserted into a subject, comprising:

a first light guide member that guides light with a first wavelength;

a first light emitting portion from which the light guided by the first light guide member is emitted;

a second light guide member that is provided so as to be adjacent to the first light guide member and guides light with a second wavelength different from the first wavelength;

a second light emitting portion from which the light guided by the second light guide member is emitted;

a light absorption/conversion member that at least partially covers light emission surfaces of the first light emitting portion and the second light emitting portion, absorbs the light with the first wavelength emitted from the first light emitting portion to generate photoacoustic waves, and converts the light with the second wavelength emitted from the second light emitting portion into light with a third wavelength different from the first wavelength and the second wavelength; and a transparent resin that transmits the light with the third wavelength, wherein the insert is a puncture needle having an inner cavity, the insert further includes a hollow tube in which the first light guide member and the second light guide member are accommodated, and the first light guide member, the second light guide member, and the light absorption/conversion member are fixed to an inner wall of the hollow tube by the transparent resin.

9. The photoacoustic image generation apparatus according to claim 5, wherein the photoacoustic image generation unit generates a third photoacoustic image on the basis of both the first photoacoustic waves and the second photoacoustic waves.

10. The photoacoustic image generation apparatus according to claim 9, further comprising:

image combination unit that combines at least one of the first photoacoustic image, the second photoacoustic image, or the third photoacoustic image and the reflected acoustic image.

* * * * *